United States Patent [19]

Hashimoto et al.

[11] 4,334,108

[45] Jun. 8, 1982

[54] PROCESS AND APPARATUS FOR PREPARATION OF PHENOLS

[75] Inventors: Katsuhiko Hashimoto; Hirohiko Nambu, both of Iwakuni; Kazuhiro Watari, Waki; Kenichi Mizuno, Iwakuni; Tadateru Murakami, Otake; Yutaka Matsuoka, Iwakuni; Mitsutoshi Moriyama, Musashino; Norio Ohno, Waki, all of Japan

[73] Assignee: Mitsu Petrochemical Industries Ltd., Tokyo, Japan

[21] Appl. No.: 164,147

[22] Filed: Jun. 30, 1980

[30] Foreign Application Priority Data

Jun. 30, 1979 [JP] Japan .................................. 54-82019

[51] Int. Cl.³ ............................................. C07C 37/60
[52] U.S. Cl. ..................................... 568/803; 568/741; 568/771
[58] Field of Search ................. 568/771, 800, 803, 741

[56] References Cited

U.S. PATENT DOCUMENTS

| | | |
|---|---|---|
| 3,600,447 | 9/1971 | Vesely et al. ....................... 568/771 |
| 4,072,722 | 2/1978 | Umemura et al. .................. 568/771 |
| 4,078,006 | 3/1978 | Umemura et al. .................. 568/771 |

FOREIGN PATENT DOCUMENTS 723454 2/1955 United Kingdom ................ 568/771
724224 2/1955 United Kingdom ................ 568/803
910735 11/1962 United Kingdom ................ 568/771

*Primary Examiner*—Werren B. Lone
*Attorney, Agent, or Firm*—Sherman & Shalloway

[57] ABSTRACT

Disclosed is a process for the preparation of phenols which comprises reacting an α-hydroxyalkyl-substituted aromatic compound and/or an α,β-unsaturated alkyl-substituted aromatic compound with hydrogen peroxide in the presence of an acid catalyst, in which hydrogen peroxide is diluted with a diluent, especially acetone, so that the volume is at least 10 times the original volume, and the diluted hydrogen peroxide is supplied in a divided manner to at least two portions of a reaction vessel or the diluted hydrogen peroxide is scattered by sprinkling into the reaction vessel. According to a preferred embodiment, the diluted hydrogen peroxide is continuously supplied to the gas phase in the reaction vessel from a scattering device which is similar to but separate from a scattering device for supplying the starting aromatic compound, particularly, a product formed by oxidizing an isopropyl aromatic compound with molecular oxygen.

According to this process, the efficiency of utilization of hydrogen peroxide is increased and a phenol of high quality can be obtained in a high yield with a high safety.

10 Claims, 4 Drawing Figures

Fig. I

PROCESS AND APPARATUS FOR PREPARATION OF PHENOLS

BACKGROUND OF THE INVENTION (1) Field of the Invention

The present invention relates to a process and apparatus for preparing phenols from α-hydroxyalkyl-substituted aromatic compounds and/or α,β-unsaturated alkyl-substituted aromatic compounds.

(2) Description of the Prior Art

It is known that when an α-hydroxyalkyl-substituted aromatic compound (often called "aromatic compound" hereinafter) and/or an α,β-unsaturated alkyl-substituted aromatic compound (often called "aromatic unsaturated compound" hereinafter) is reacted with hydrogen peroxide in the presence of an acidic catalyst, a phenol is formed (see, for example, the specification of British Pat. No. 910,735). Since such aromatic alcohol or aromatic unsaturated compound is formed as a by-product when an alkyl aromatic compound is oxidized to a corresponding hydroperoxide with molecular oxygen, when a phenol is prepared by acid decomposition of the so formed hydroperoxide, the yield based on the starting alkyl aromatic compound will be increased if this by-product can be converted to the phenol. Accordingly, this process utilizing the above-mentioned reaction with hydrogen peroxide is very attractive. However, since hydrogen peroxide is a strong oxidant, the once formed phenol is reacted with this hydrogen peroxide, resulting in reduction of the yield of the phenol or degradation of the quality of the phenol due to formation of coloring impurities. Especially, when the volume of the reaction vessel is increased, it becomes difficult to advance the intended reaction at a high efficiency while controlling undesired side reactions.

BRIEF SUMMARY OF THE INVENTION

The present inventors have conducted research with a view to developing a process for preparing phenols of high quality at high yields with high safety while overcoming the above-mentioned defects. The present invention resulted from such research.

In accordance with the present invention, there is provided a process for the preparation of phenols which comprises reacting an α-hydroxyalkyl-substituted aromatic compound and/or an α,β-unsaturated alkyl-substituted aromatic compound with hydrogen peroxide in the presence of an acid catalyst, wherein hydrogen peroxide is diluted with a diluent so that the volume is at least 10 times the original volume, and the diluted hydrogen peroxide is supplied in a divided manner to at least two portions of a reaction vessel or the diluted hydrogen peroxide is scattered into the reaction vessel by sprinkling.

BRIEF DESCRIPTION OF THE DRAWINGS

In the accompanying drawings.

Figure 1:
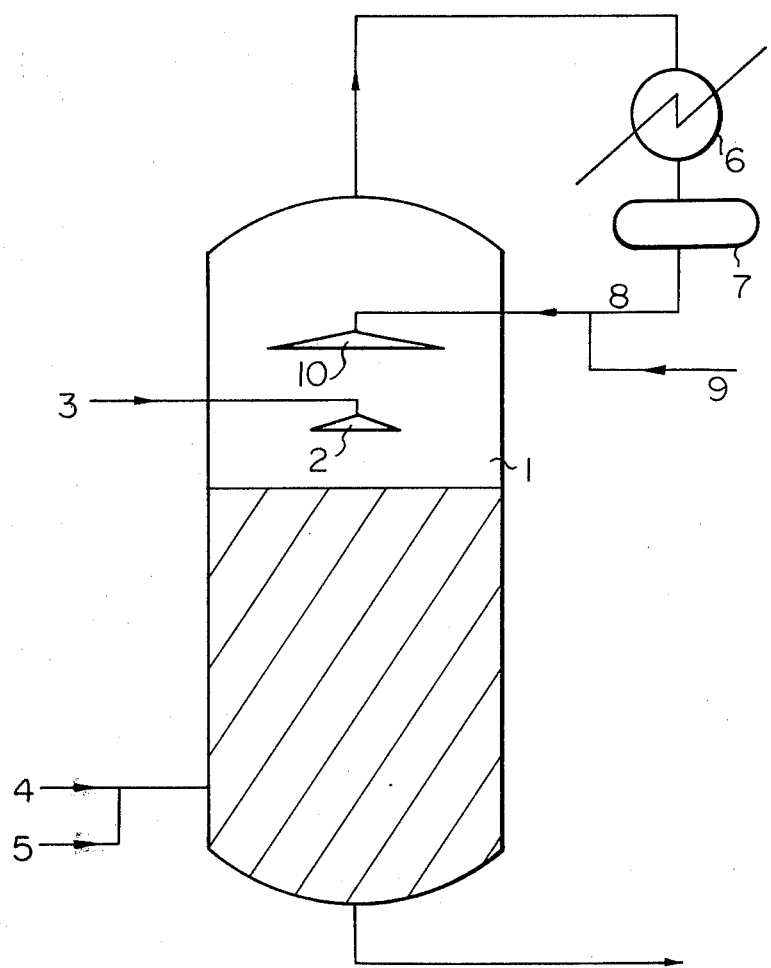
FIG. 1 is a diagram illustrating one embodiment of the reaction vessel used for carrying out the process of the present invention.

In the drawings, reference numerals, 1, 2, 6, 7, 10, 12, 15 and 18 represent a reaction vessel, a perforated plate, a condenser, a drum, a perforated plate, a spray pipe, a scattering nozzle and a diluent feed pipe, respectively.

DETAILED DESCRIPTION OF THE PREFERRED EMBODIMENTS

Typical instances of the aromatic alcohol that can be used in the present invention as the starting material are represented by the following general formula:

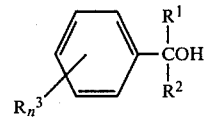

wherein $R^1$ and $R^2$ stand for a hydrogen atom or an alkyl group, preferably an alkyl group having 1 to 3 carbon atoms, $R^3$ stands for a hydrogen atom, an alkyl group,

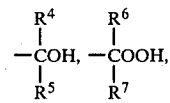

a halogen atom, —OH,

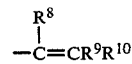

or

in which $R^4$, $R^5$, $R^6$, $R^7$, $R^8$, $R^9$ and $R^{10}$ stand for a hydrogen atom or an alkyl group and $R^{11}$ stands for an alkyl group, and n is an integer of from 1 to 5 with the proviso that n of groups $R^3$ may be the same or different.

As specific examples of such aromatic alcohol, there can be mentioned α-methylbenzyl alcohol, α-ethylbenzyl alcohol, α,α-dimethylbenzyl alcohol, α-methyl-α-ethylbenzyl alcohol, α,α-diethylbenzyl alcohol, α-methyl-p-methylbenzyl alcohol, α-methyl-m-methylbenzyl alcohol, α,α-dimethyl-p-methylbenzyl alcohol, α,α-dimethyl-m-methylbenzyl alcohol, α,α-dimethyl-p-isopropylbenzyl alcohol, α,α-dimethyl-,-isopropylbenzyl alcohol, α,α-dimethyl-p-isopropenylbenzyl alcohol, α,α-dimethyl-m-isopropenylbenzyl alcohol, α,α'-dihydroxy-p-diisopropylbenzene, α,α'-dihydroxy-m-diisopropylbenzene, α,α-dimethyl-p-hydroxybenzyl alcohol, α,α-dimethyl-m-hydroxybenzyl alcohol, α,α-dimethyl-m-chlorobenzyl alcohol, α-hydroxy-α'-hydroperoxy-p-diisopropylbenzene and α-hydroxy-α'-hydroperoxy-m-diisopropylbenzene.

Typical instances of the aromatic unsaturated compound that is used in the present invention are represented by the following general formula:

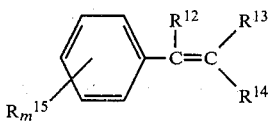

wherein $R^{12}$, $R^{13}$ and $R^{14}$ represent a hydrogen atom or an alkyl group, $R^{15}$ stands for a hydrogen atom, an alkyl group,

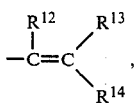

a halogen atom,

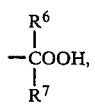

—OH or

and m is an integer of from 1 to 5 with the proviso that each of groups $R^{15}$ may be the same or different.

As specific examples of such aromatic unsaturated compound, there can be mentioned α-methylstyrene, α-ethylstyrene, β-methylstyrene, isopropenyltoluene, isopropenylethylbenzene, isopropenylcumene, diisopropenylbenzene and isopropenylphenol. Mixtures of two or more of these compounds may be used.

In the present invention, a starting material containing the above-mentioned aromatic alcohol and/or aromatic unsaturated compound is used. The starting material may further contain other components. For example, the starting material may contain a hydroperoxide of an alkyl aromatic compound, such as cumene hydroperoxide, m-cymene hydroperoxide, p-cymene hydroperoxide, m-diisopropylbenzene monohydroperoxide, p-diisopropylbenzene monohydroperoxide, m-diisopropylbenzene dihydroperoxide or p-diisopropylbenzene dihydroperoxide. The starting material may also contain a hydrocarbon such as benzene, toluene, xylene, ethylbenzene, cumene, cymene or diisopropylbenzene and a ketone such as acetone, methylethyl ketone, diethyl ketone or methylisobutyl ketone. A reaction product obtained by oxidizing an alkyl aromatic compound with molecular oxygen and condensing the reaction mixture according to need contains not only a hydroperoxide of an alkyl aromatic compound but also an aromatic alcohol or aromatic unsaturated compound. Accordingly, this reaction product can be preferably used as the starting material in the present invention. When this starting material is reacted with hydrogen peroxide at the acid decomposition step, side reactions are readily caused to occur. However, if the conditions of the present invention are adopted, occurrence of side reactions can be controlled and the intended reaction can be advanced effectively.

Various acid catalysts may be used in the present invention. For example, there can be mentioned inorganic acids such as sulfuric acid, phosphoric acid, perchloric acid and hydrochloric acid, solid acids such as silica-alumina, molybdic acid and phosphomolybdic acid, organic acids such as toluene-sulfonic acid and trichloroacetic acid, and ion exchange resins.

The amount used of the acid catalyst is changed according to the kind thereof and the water content in the starting reaction mixture, and it cannot be simply determined. However, if a liquid acid catalyst is employed, it is preferred that the amount of the acid catalyst be about 0.01 to about 10% by weight, especially about 0.1 to about 3.0% by weight, based on the reaction medium.

In the present invention, by supplying hydrogen peroxide to the reaction system, the aromatic alcohol and/or aromatic unsaturated compound is converted to a corresponding phenol. In the present invention, hydrogen peroxide is diluted so that the volume is at least 10 times, preferably 15 to 100 times, the original volume, and hydrogen peroxide is supplied in the thus diluted state. If a large amount of water is present in the starting reaction mixture, it is necessary to use a large amount of the acid catalyst. Accordingly, hydrogen peroxide is diluted with a diluent other than water. For example, acetone which can be used as a reaction solvent, has a good compatibility with hydrogen peroxide and can be removed by evaporation is a most preferred diluent. When hydrogen peroxide is diluted with acetone, it is preferred that the reaction be carried out under reflux of acetone so as to remove the reaction heat and hydrogen peroxide be diluted with refluxed acetone. Of course, when other reaction solvent is used, this solvent may also be used as the diluent for hydrogen peroxide. Moreover, the starting material containing the aromatic alcohol and/or aromatic unsaturated compound can be used as the diluent by itself.

In each case, from a safety viewpoint, it is preferred that hydrogen peroxide be diluted with such organic compound just before it is supplied to the starting liquid mixture.

The diluted hydrogen peroxide is supplied in a divided manner to at least 2 portions of a reaction vessel or it is scattered into the reaction vessel in a sprinkling manner. For example, there can be adopted a method in which the diluted hydrogen peroxide is supplied into the reaction vessel from at least two feed openings, a method in which a stirrer having many agitation vanes is used and the diluted hydrogen peroxide is supplied from parts of the agitation vanes and a method in which a perforated plate is disposed in the upper portion of the reaction vessel and the diluted hydrogen peroxide is supplied and sprinkled through this perforated plate. The method in which the diluted hydrogen peroxide is sprinkled from the upper portion of the reaction vessel is especially preferred. If there is adopted a method in which hydrogen peroxide is supplied from one portion at a time, it is difficult to increase the yield of the resulting phenol, and reduction of the quality of the phenol is often caused.

It is preferred that the amount of hydrogen peroxide be smaller than the amount equimolar to the sum of the alcoholic hydroxyl group of the secondary alcohol, and the tertiary alcohol and the olefinic double bond in the α-hydroxyalkyl-substituted aromatic compound and/or α,β-unsaturated alkyl-substituted aromatic compound. If the amount of hydrogen peroxide exceeds this critical level, hydrogen peroxide is used for oxidation of the formed phenol or the ketone, resulting in reduction of the efficiency of utilization of hydrogen peroxide or occurrence of undesired phenomena such as lowering of the purity of the formed phenol.

The reaction is ordinarily carried out under agitation. The reaction temperature is ordinarily in the range of 20° to 100° C. and preferably in the range of 40° to 90° C. It is preferred that the reaction be conducted in a continuous manner, and the residence time is ordinarily in the range of 1 minute to 2 hours and preferably in the range of about 5 minutes to about 1 hour.

In accordance with one preferred embodiment of the present invention, there is provided a process for the preparation of phenols, which comprises the steps of (i) supplying a starting material containing a hydroperoxide of an isopropyl aromatic compound and an α-hydroxypropyl-substituted aromatic compound and/or α,β-unsaturated isopropenyl-substituted aromatic compound, which is obtained by oxidizing an isopropyl aromatic compound, especially diisopropylbenzene or cymene, with molecular oxygen, to a liquid phase reaction mixture containing an acid catalyst and acetone by scattering the starting material from a first scattering device located in the gas phase above said reaction mixture, (ii) supplying a dilution of hydrogen peroxide, which is formed by diluting hydrogen peroxide with acetone so that the volume is 10 to 100 times the original volume, into said reaction mixture by scattering said dilution into said reaction mixture from a second scattering device located in the gas phase above said reaction mixture, (iii) contacting the starting material, hydrogen peroxide and acid catalyst with one another under a condition distilling off acetone from the reaction mixture, (iv) circulating the distilled acetone as a diluent to the step (ii), and (v) recovering the formed phenol from the reaction mixture.

In this embodiment, it is preferred that the second scattering device be located at a position higher than the position of the first scattering device, and that the acetone dilution of hydrogen peroxide and the starting material be continuously scattered through said second scattering device and said first scattering device, respectively.

For example, a scattering device disclosed in the specification of U.S. Pat. No. 3,271,457 can be used as the second scattering device. In the process disclosed in this U.S. patent specification, an alkaryl hydroperoxide is mixed with acetone in advance and the mixture is scattered in the reaction system. Accordingly, the process of the present invention is different from this known process in the point where hydrogen peroxide is diluted with acetone and the dilution is scattered independently from the starting aromatic compound.

From the viewpoints of the efficiency of utilization of hydrogen peroxide and the operation safety, in the present invention, it is most advantageous and preferred that a scattering device comprising an annular acetone feed pipe having an opening in the lower portion thereof and many hydrogen peroxide feed nozzles, each having the top end located at the substantially same position as that of said opening, be used as the second scattering device and hydrogen peroxide falling down from said nozzles be diluted with a large quantity of acetone.

Figure 2:
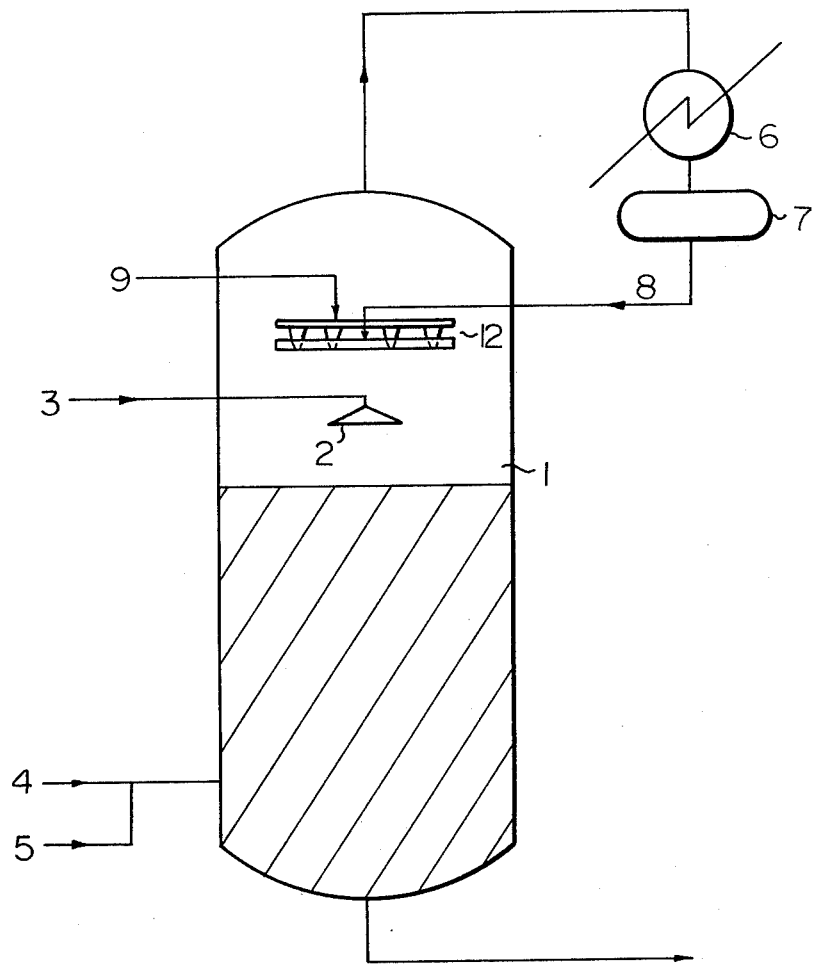
FIG. 2 is a diagram illustrating another embodiment of the reaction vessel.

FIGS. 1 and 2 are diagrams illustrating embodiments in which an oxidation product of p-diisopropylbenzene is acid-decomposed in acetone as the solvent in the presence of hydrogen peroxide.

Referring to FIG. 1, the oxidation product of p-diisopropylbenzene is continuously supplied from a scattering device 2 located in the upper portion of a reaction vessel 1 through a pipe 3. Sulfuric acid acting as the catalyst is continuously supplied from a pipe 4 and acetone acting as the solvent is continuously supplied from a pipe 5. The reaction heat is removed by evaporation of acetone, and evaporated acetone is condensed in a condenser 6 and after this acetone is once stored in a drum 7, it is introduced through a pipe 8 and mixed with hydrogen peroxide introduced into the pipe 8 through a pipe 9. The mixture is scattered from a scattering device 10.

In this embodiment, it is preferred that the scattering devices 2 and 10 be different in the diameter as shown in FIGS. 1 and 2, and it is especially preferred that the diameter of the scattering device 2 be smaller than the diameter of the scattering device 10. In this case, mingling of the dilution of hydrogen peroxide and the stream of the oxidation product of p-diisopropylbenzene is substantially prevented in the gas phase.

The embodiment shown in FIG. 2 is different from the embodiment shown in FIG. 1 only in the manner of feeding and scattering hydrogen peroxide, and in other points, both the embodiments are identical.

Figure 3:
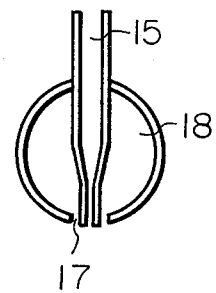
FIGS. 3 and 4 are diagrams illustrating nozzles for feeding hydrogen peroxide.
Figure 4:
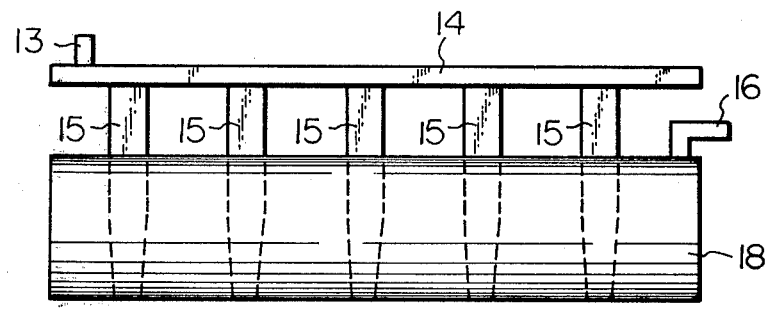

FIGS. 3 and 4 are diagrams illustrating in detail the scattering pipe 12 shown in FIG. 2. Hydrogen peroxide is introduced into a hydrogen peroxide-scattering annular pipe 14 from a nozzle 13 and supplied in a divided manner into many scattering nozzles 15. Refluxed acetone is supplied to an acetone-supplying annular pipe 18 having an opening 17 in the lower portion thereof from a nozzle 16. Since the top end of each scattering nozzle 15 is located at the position of the opening 17 of the acetone feed pipe 18, when hydrogen peroxide falls down from the scattering nozzles 15, it is diluted with a large quantity of acetone. If this scattering device is employed, hydrogen peroxide is incorporated just before entrance into the reaction vessel, and the operation can be conducted very safely.

The present invention will now be described in detail with reference to the following Examples that by no means limit the scope of the invention.

EXAMPLE 1

A reaction vessel as shown in FIG. 2, which had an inner capacity of 50 liters, was used. A methylisobutyl ketone (MIBK) solution of an oxidation product of p-diisopropylbenzene, which contained 24% by weight of α,α'-dihydroperoxy-p-diisopropylbenzene (p-DHP) and 9.5% by weight of α-hydroperoxy-α'-hydroxy-p-diisopropylbenzene (p-HHP), was supplied into the reaction vessel at a rate of 35 l/hr from a perforated plate 2 through a pipe 3. A 60% aqueous solution of hydrogen peroxide was supplied into the reaction vessel at a rate of 0.53 l/hr (0.66 Kg/hr) from a scattering plate 12 through a pipe 9 and acetone containing 3% by weight of sulfuric acid was supplied into the reaction vessel from pipes 4 and 5 at a rate of 9.5 l/hr. The hydrogen peroxide/alcoholic hydroxyl group molar ratio was 0.74. Reaction was carried out with stirring under atmospheric pressure and reflux of acetone (74° C.). The refluxed acetone was passed through a condenser 6 and a drum 7 at a rate of about 26 Kg/hr and was returned to the reaction vessel from a pipe 8 while diluting hydrogen peroxide fed through the scattering plate 12. The liquid reaction mixture was continuously withdrawn from the reaction system by overflowing so that the residence time was 30 minutes. The concentration of hydroquinone (HQ) in the obtained liquid reaction mixture was 12.5% by weight, which corresponded to a yield of 136% based on p-DHP and also to a yield of 95.5% based on the sum of p-DHP and p-HHP. The ratio (%) of effective utilization of hydrogen peroxide, which was calculated according to the following formula:

$$\frac{[(\text{mols of formed HQ}) - (\text{mols of fed p-DHP})]}{(\text{mols of fed H}_2\text{O}_2)} \times 100$$

was 100%.

The obtained liquid reaction mixture was neutralized, and acetone, water and MIBK were removed by distillation, and hydroquinone was extracted with water and then extracted with MIBK. The crystal of hydroquinone left after distillation of MIBK was substantially colorless. The absorbance (determined by using a 5-mm cell) of a solution containing 5% by weight of this hydroquinone in MIBK at 420 m$\mu$ was 0.075.

EXAMPLE 2

Reaction was carried out in the same manner as described in Example 1 except that the feed rates of the respective starting materials were changed as follows:
MIBK solution of oxidation product of p-diisopropylbenzene: 35 l/hr
60% aqueous solution of hydrogen peroxide: 0.67 l/hr (0.83 Kg/hr)
Acetone solution containing 3% of sulfuric acid: 9.7 l/hr
Refluxed acetone: about 33 Kg/hr
Hydrogen peroxide/alcoholic hydroxyl group molar ratio: 0.92

The concentration of hydroquinone in the obtained liquid reaction mixture was 12.9%, which corresponded to a yield of 141% based on p-DHP and also to a yield of 99.0% based on the sum of p-DHP and p-HHP. The ratio of effective utilization of hydrogen peroxide was 90%. The liquid reaction mixture was treated in the same manner as described in Example 1. The obtained crystal of hydroquinone was substantially colorless, and the absorbance of a solution containing 5% by weight of this hydroquinone in MIBK at 420 m$\mu$ was 0.085.

EXAMPLE 3

Reaction was carried out in the same manner as described in Example 1 except that a reaction vessel having an inner capacity of 50 liters and a structure shown in FIG. 1 was used as the reaction vessel. The concentration of hydroquinone in the obtained liquid reaction mixture was 12.4% by weight, which corresponded to a yield of 135% based on p-DHP and also to a yield of 94.7% based on the sum of p-DHP and p-HHP. The ratio of effective utilization of hydrogen peroxide was 97%.

COMPARATIVE EXAMPLE 1

A reaction vessel having an inner capacity of 50 liters, which was constructed by modifying the reaction vessel shown in FIG. 2 so that hydrogen peroxide was directly introduced into the reaction mixture from the pipe 9 without passage through the scattering plate 12 was used, and reaction was carried out in the same manner as described in Example 1. The concentration of hydroquinone in the obtained liquid reaction mixture was 11.0% by weight, which corresponded to a yield of 120% based on p-DHP and also to a yield of 84.1% based on the sum of p-DHP and p-HHP. The ratio of effective utilization of hydrogen peroxide was reduced to 55%. The obtained liquid reaction mixture was treated in the same manner as described in Example 1. The obtained hydroquinone crystal was considerably reddish, and a 5% by weight solution of this hydroquinone in MIBK had an absorbance as high as 0.37 at 420 m$\mu$.

COMPARATIVE EXAMPLE 2

A reaction vessel having an inner capacity of 50 liters, which was constructed by modifying the reaction vessel shown in FIG. 1 so that the perforated plate 10 was removed and the mixture of hydrogen peroxide and refluxed acetone was directly introduced into the reaction mixture from the pipe 8 or 9, was used as the reaction vessel. Reaction was carried out in the same manner as described in Example 1.

The concentration of hydroquinone in the obtained reaction mixture was 11.5% by weight, which corresponded to a yield of 125% based on p-DHP and also to a yield of 87.9% based on the sum of p-DHP and p-HHP. The ratio of effective utilization of hydrogen peroxide was 70%. The hydroquinone crystal obtained by treating the liquid reaction mixture in the same manner as described in Example 1 had a yellowish red color, and a 5% by weight solution of this hydroquinone in MIBK had an absorbance of 0.21 at 420 m$\mu$.

EXAMPLE 4

A reaction vessel as shown in FIG. 2, which had an inner capacity of 50 liters, was used. An oxidation product of a mixture of m-cymene and p-cymene, which contained 68.8% by weight of a mixture of m- and p-cymene hydroperoxides, 9.3% by weight of a mixture of m- and p-tertiary alcohols and 2.2% by weight of a mixture of m- and p-primary alcohols, was supplied into the reaction vessel at a rate of 70 l/hr from a perforated plate 2 through a pipe 3. A 60% aqueous solution of hydrogen peroxide was supplied into the reaction vessel at a rate of 1.47 l/hr (1.82 Kg/hr) from a scattering plate through a pipe 9, and acetone containing 1.78% by weight of sulfuric acid was supplied into the reaction vessel at a rate of 22 l/hr from pipes 4 and 5. The hydrogen peroxide/tertiary alcohol molar ratio was 0.74. Reaction was carried out with stirring under atmospheric pressure and reflux of acetone (78° C.). The circulation ratio of refluxed acetone was about 70 Kg/hr. The liquid reaction mixture was continuously withdrawn from the reaction system by overflowing so that the residence time was 15 minutes.

The concentration of a mixture of m- and p-cresols in the obtained liquid mixture was 30% by weight, which corresponded to a yield of 86.3% based on the mixture of m- and p-cymene hydroperoxides. The ratio (%) of effective utilization of hydrogen peroxide, which was calculated according to the following formula:

$$\frac{[(\text{mols of formed cresols}) - (\text{molds of fed cymene hydroperoxides})]}{(\text{mols of fed H}_2\text{O}_2)} \times 100$$

was 77%.

What we claim is:
1. In a process for the preparation of phenols which comprises reacting an $\alpha$-hydroxyalkyl-substituted aromatic compound and/or an $\alpha,\beta$-unsaturated alkyl-substituted aromatic compound with hydrogen peroxide in the presence of an acid catalyst, at a temperature of 20° to 100° C., the improvement wherein the hydrogen peroxide is diluted with a diluent comprising acetone so that the volume is 10 to 100 times the original volume, and the diluted hydrogen peroxide is supplied in a divided manner to at least two portions of the reaction vessel.

2. A process for the preparation of phenols according to claim 1 wherein the reaction is carried out under reflux of acetone and hydrogen peroxide is diluted with refluxed acetone.

3. A process for the preparation of phenols according to claim 1 wherein hydrogen peroxide is used in an amount smaller than the amount equimolar to the sum of the alcoholic hydroxyl group of a secondary alcohol, the alcoholic hydroxyl group of a tertiary alcohol and the olefinic double bond in the α-hydroxyalkyl-substituted aromatic compound and/or the α,β-unsaturated alkyl-substituted aromatic compound.

4. A process for the preparation of phenols, which comprises the steps of (i) supplying a starting material containing a hydroperoxide of an isopropyl aromatic compound and an α-hydroxypropyl-substituted aromatic compound and/or α,β-unsaturated isopropenyl-substituted aromatic compound, which is obtained by oxidizing an isopropyl aromatic compound with molecular oxygen, to a liquid phase reaction mixture containing an acid catalyst and acetone by scattering the starting material from a first scattering device located in the gas phase above said reaction mixture, (ii) supplying a dilution of hydrogen peroxide, which is formed by diluting hydrogen peroxide with acetone so that the volume is 10 to 100 times the original volume, into said reaction mixture by scattering said dilution into said reaction mixture from a second scattering device located in the gas phase above said reaction mixture, (iii) contacting the starting material, hydrogen peroxide and acid catalyst with one another under a condition of distilling off acetone from the reaction mixture, (iv) circulating the distilled acetone as a diluent to step (ii), and (v) recovering the formed phenol from the reaction mixture.

5. A process for the preparation of phenols according to claim 4 wherein said second scattering device is located at a position higher than the position of the first scattering device, and the acetone dilution of hydrogen peroxide and the starting material are continuously scattered through said second scattering device and said first scattering device, respectively.

6. A process for the preparation of phenols according to claim 4 or 5 wherein a scattering device comprising an annular acetone feed pipe having an opening in the lower portion thereof and many hydrogen peroxide feed nozzles, each having the top end located at the substantially same position as that of said opening, is used as the second scattering device and hydrogen peroxide falling down from said nozzles is diluted with a large quantity of acetone.

7. A process for the preparation of phenols according to claim 4 wherein the isopropyl aromatic compound is diisopropylbenzene or cymene.

8. In a process for the preparation of phenols which comprises reacting an α-hydroxyalkyl-substituted aromatic compound and/or an α,β-unsaturated alkyl-substituted aromatic compound with hydrogen peroxide in the presence of an acid catalyst, at a temperature of 20° to 100° C., the improvement wherein hydrogen peroxide is diluted with a diluent comprising acetone so that the volume is 10 to 100 times the original volume, and the diluted hydrogen peroxide is scattered by sprinkling the same into the reaction vessel.

9. A process for the preparation of phenols according to claim 8 wherein the reaction is carried out under reflux of acetone and hydrogen peroxide is diluted with refluxed acetone.

10. A process for the preparation of phenols according to claim 8 wherein hydrogen peroxide is used in an amount smaller than the amount equimolar to the sum of the alcoholic hydroxyl group of a secondary alcohol, the alcoholic hydroxyl group of a tertiary alcohol and the olefinic double bond in the α-hydroxyalkyl-substituted aromatic compound and/or the α-β-unsaturated alkyl-substituted aromatic compound.

* * * * *

UNITED STATES PATENT AND TRADEMARK OFFICE
CERTIFICATE OF CORRECTION

PATENT NO. : 4,334,108
DATED : June 8, 1982
INVENTOR(S) : HASHIMOTO, ET AL.

It is certified that error appears in the above—identified patent and that said Letters Patent is hereby corrected as shown below:

Cover page, item [73] should read as follows:

Assignee: Mitsui Petrochemical Industries Ltd., Tokyo, JApan

Signed and Sealed this

Tenth Day of August 1982

[SEAL]

Attest:

Attesting Officer

GERALD J. MOSSINGHOFF
Commissioner of Patents and Trademarks